United States Patent
Cananzey et al.

[11] Patent Number: 5,470,317
[45] Date of Patent: Nov. 28, 1995

[54] SWIVEL BARREL ASSEMBLY FOR INFLATION SYRINGE

[75] Inventors: John J. Cananzey, Charlestown; Scot M. Lucey, Newbury, both of N.H.

[73] Assignee: Design Standards Corporation, Charlestown, N.H.

[21] Appl. No.: 284,303

[22] Filed: Aug. 2, 1994

[51] Int. Cl.$^6$ .................................................. A61M 1/00
[52] U.S. Cl. ........................... 604/121; 604/100; 604/118
[58] Field of Search ................... 604/99, 100, 121, 604/211, 187, 188; 128/919

[56] References Cited

U.S. PATENT DOCUMENTS

| | | | |
|---|---|---|---|
| 2,267,798 | 11/1975 | Hartalides | 604/211 |
| 4,457,712 | 7/1984 | Dragan | 433/90 |
| 4,743,230 | 5/1988 | Nordquest | 604/97 |
| 4,832,692 | 5/1989 | Box et al. | 604/99 |
| 4,919,121 | 4/1990 | Rydell et al. | 604/97 |
| 5,137,514 | 8/1992 | Ryan | 604/99 |
| 5,137,514 | 8/1992 | Ryan . | |
| 5,213,115 | 5/1993 | Zytkovicz et al. | 128/898 |

*Primary Examiner*—C. Fred Rosenbaum
*Assistant Examiner*—Bryan L. Tsosie
*Attorney, Agent, or Firm*—Bachman & LaPointe

[57] ABSTRACT

The invention relates to an inflation syringe assembly, which includes a housing having a barrel portion defining an interior space; a pressure gauge mounted to the barrel portion; a plunger disposed in the barrel portion; and structure for advancing the plunger in the barrel portion, wherein the barrel portion is rotatable relative to the housing so that the barrel portion with the pressure gauge is rotatable to a desired position relative to the housing.

14 Claims, 1 Drawing Sheet

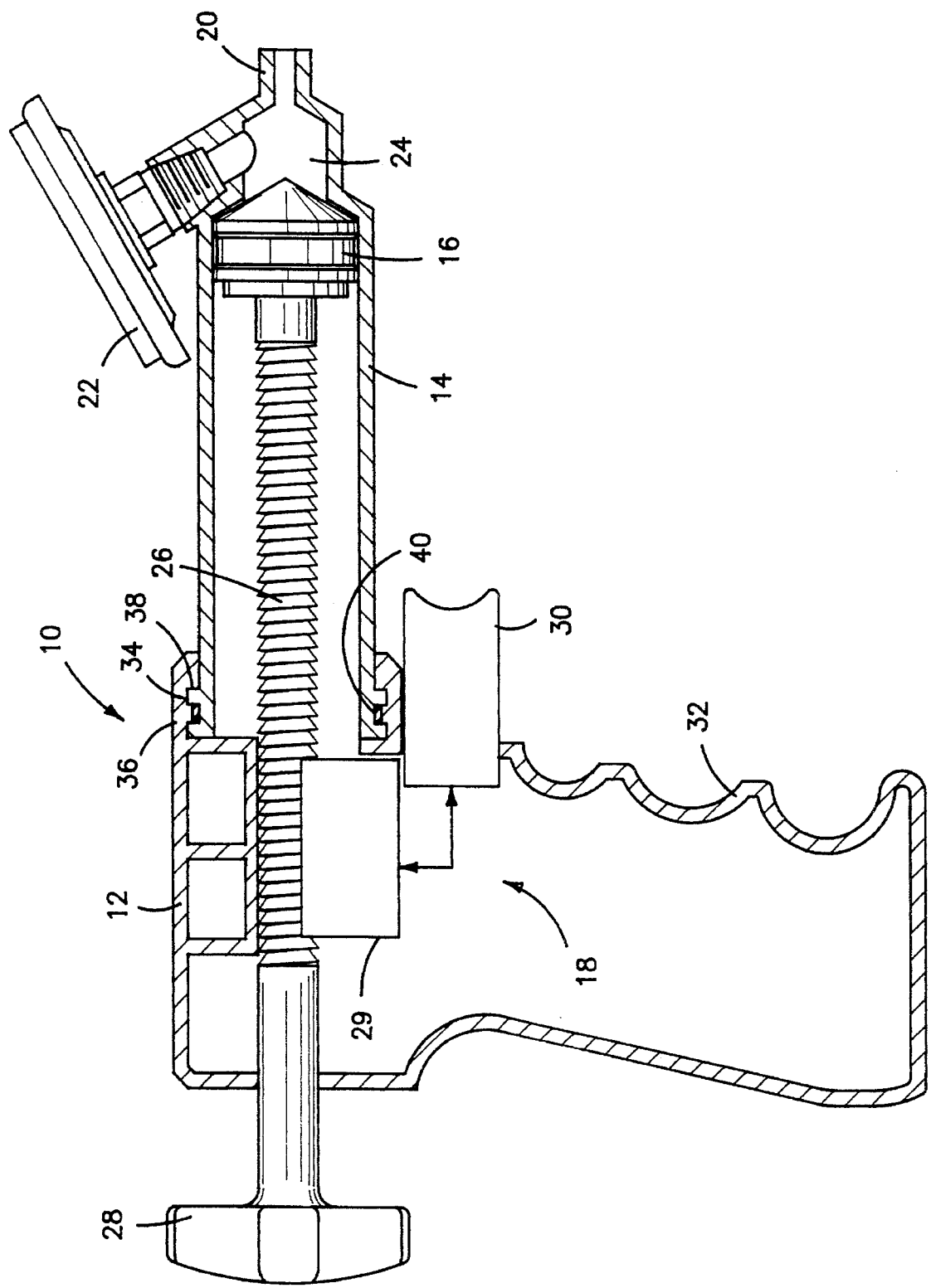

SWIVEL BARREL ASSEMBLY FOR INFLATION SYRINGE

BACKGROUND OF THE INVENTION

The invention relates to a swivel assembly for an inflation syringe such as those typically used for procedures such as percutaneous transluminal angioplasty and other procedures which involve the inflation of a balloon catheter.

Syringe assemblies are typically used for inflating balloon catheters in operations which may be referred to as balloon angioplasty, wherein a catheter with a dilatible balloon at or near its tip is threaded into and through an artery to a stenotic region. The balloon is then inflated thereby compressing obstructions or other material against the artery wall so as to widen the interior diameter of the vessel and again permit sufficient flow of blood.

The balloon is typically inflated utilizing a pressurized fluid such as a mixture of equal parts of a contrast media and a saline solution which fluid is pressurized to exert the dilatation pressure on the balloon catheter. An inflation syringe assembly is typically utilized to deliver the fluid under pressure to the balloon.

U.S. Pat. No. 5,137,514 to Ryan illustrates a typical inflation syringe assembly. As shown in Ryan, the assembly typically includes a pressure gauge which is directed upwardly for reading the pressure which is being delivered to the balloon catheter. This is useful so the doctor or technician may monitor the pressure being delivered to the balloon while the procedure is being carried out.

Also as shown in the Ryan patent, such a device typically has a downwardly depending handle or grip portion which is held by the doctor or technician during the procedure. Such grip portions are useful while the syringe assembly is being held. However, when the syringe assembly must be set down during the procedure, the pistol grip renders it necessary to position the syringe assembly on its side. In this position the pressure gauge is no longer readily visible without forcing the doctor or technician to bend and/or twist so as to view the gauge which now is also on its side.

In accordance with the foregoing, it is the primary object of the present invention to provide a syringe assembly wherein the pressure gauge is visible regardless of the orientation of the pistol grip portion of the housing.

It is a further object of the invention to provide a syringe assembly which is more convenient in use.

It is a still further object of the invention to provide a syringe assembly wherein pressure is more readily monitored so as to provide safer medical and surgical procedures.

Other objects and advantages will appear hereinbelow.

SUMMARY OF THE INVENTION

In accordance with the invention, the foregoing objects and advantages are readily attained.

A syringe assembly in accordance with the invention is provided which includes a housing having a barrel portion defining an interior space; a plunger disposed in said barrel portion; and means for advancing said plunger in said barrel portion, wherein said barrel portion is rotatable relative to said housing. Indicator means such as a pressure gauge positioned on said barrel portion may advantageously be viewed regardless of the position of the housing by rotating the barrel portion to a desired position.

When the syringe assembly of the present invention is to be set down or rested, for example, upon a table or other flat structure while it is being used, the barrel of the syringe assembly is simply pivoted or swiveled so that the pressure gauge remains in an upright and therefore visible position.

BRIEF DESCRIPTION OF THE DRAWING

A detailed description of the preferred embodiments of the invention will now be described with reference to the attached drawing which illustrates a cross section of a syringe assembly in accordance with the invention.

DETAILED DESCRIPTION

The invention is drawn to an inflation syringe assembly for use in fluid pressurization of a balloon catheter and the like. The figure illustrates a syringe assembly 10 in accordance with the invention. Syringe assembly 10 includes a housing 12, a barrel portion 14, and a plunger 16 advancably disposed within barrel 14. A mechanism 18 is provided for advancing plunger 16 within barrel 14 so as to deliver fluid under pressure from an open end 20 of barrel 14. Such fluid under pressure is delivered through a tube (not shown) connected to end 20 to the balloon catheter (not shown) which is to be pressurized. In accordance with the invention, a pressure gauge 22 is arranged on barrel 14 in fluid communication with the passage 24 defined by barrel portion 14 so as to provide a reading of pressure within passage 24 and, of course, the tube and balloon catheter which are connected to passage 24 and being pressurized. Fluid is typically pressurized by advancing plunger 16 within barrel portion 14 via any of numerous known mechanisms. For example, mechanism 18 may be a threaded arrangement whereby rotation of rod 26 via knob 28 causes advance or retreat of plunger 16 within barrel portion 14. Further, mechanism 18 typically includes an engaging member 29 engagable or disengagable with rod 26, for example, via trigger means 30, all as is well known in the art.

It is also noted that housing 12 typically includes a downwardly depending pistol grip portion 32 which is used to firmly grasp syringe assembly 10 during use.

As set forth above, pistol grip 32 requires syringe assembly 10 to be laid flat or horizontally on its side when syringe assembly 10 is to be positioned upon a flat surface. Also as discussed above, however, such orientation of syringe assembly 10 renders it difficult to read pressure gauge 22.

Thus, in accordance with the present invention, barrel portion 14 is rotatably mounted or otherwise positioned within housing 12 so that pressure gauge 22 may be oriented advantageously to a position for convenient reading regardless of the position of pistol grip 32. As shown in the figure, barrel portion 14 may preferably have one or more radially extending ridges 34, and housing 12 may suitably have a collar portion 36 which defines one or more circumferential inner grooves 38 in which ridges 34 of barrel portion 14 are received. Ridges 34 and grooves 38 are preferably selected to snugly engage one another so as to allow rotation of barrel portion 14 relative to housing 12 while maintaining a seal therebetween so as to prevent loss of fluid. In this regard, one or more seal members 40 may be disposed between barrel portion 14 and housing 12 so as to improve the desired seal therebetween against fluid loss. In this manner, barrel 14 and housing 12 in accordance with the invention are sealingly and rotatably connected.

It should be noted that, while the drawing shows a specific structure for providing rotation of barrel 14 relative to housing 12, numerous other configurations may be used to provide the desired rotatable mounting in accordance with the invention.

In accordance with the foregoing, it should be readily apparent that syringe assembly 10 may be utilized with grip portion 32 in a substantially horizontal position while pressure gauge member 22 attached to rotatable barrel portion 14 is nevertheless advantageously positioned in an upright position for ease in reading. Thus, and advantageously, syringe assembly 10 may be utilized in any orientation without inhibiting the monitoring of pressure delivered to the balloon catheter. In other words, pressure gauge 22 on rotatable barrel portion 14 may be rotated independently of housing 12 to any desired position so as to enhance visibility of the readings provided by pressure gauge 22. In accordance with the foregoing, it is readily apparent that the syringe assembly disclosed in accordance with the invention readily. accomplishes the above-described objects and advantages.

It is apparent that there has been provided in accordance with this invention a swivel barrel assembly for an inflation syringe which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. An inflation syringe assembly, comprising:

a housing having a barrel portion having a longitudinal axis and defining an interior space;

means for mounting said barrel portion to said housing for rotation of said barrel portion around said axis relative to said housing without longitudinal movement of said barrel portion along said axis relative to said housing;

a plunger disposed in said barrel portion; and means associated with said housing for advancing said plunger in said barrel portion, wherein said barrel portion is rotatable relative to said housing without longitudinal movement of said barrel portion along said axis relative to said housing and said plunger.

2. A syringe assembly according to claim 1, further comprising an indicia member positioned on said barrel portion whereby rotation of said barrel portion relative to said housing positions said indicia member for viewing.

3. A syringe assembly according to claim 2, wherein said indicia member is a pressure gauge connected to said barrel portion and communicating with said interior space.

4. A syringe assembly according to claim 2, wherein said housing has a grip portion depending angularly with respect to said axis of said barrel portion.

5. A syringe assembly according to claim 4, wherein said indicia member is a pressure gauge connected to said barrel portion and communicating with said interior space.

6. A syringe assembly according to claim 1, wherein said housing has a collar for receiving said barrel portion and defining a circumferential groove lying in a single plane substantially perpendicular to said axis of said barrel portion and wherein said barrel portion has a radially outwardly directed flange positioned in said groove whereby said barrel portion is rotatable relative to said housing.

7. A syringe assembly according to claim 6, wherein said collar defines a plurality of ridges and wherein said barrel portion has a plurality of outwardly directed flanges whereby said barrel portion and said housing are substantially sealingly connected.

8. A syringe assembly according to claim 6, further comprising sealing means for sealingly connecting said barrel portion and said housing.

9. A syringe assembly according to claim 8, wherein said sealing means comprises a seal member disposed between said barrel portion and said housing.

10. An inflation syringe assembly, comprising:

a housing;

a barrel member defining an interior space;

a pressure gauge mounted on said barrel member and communicating with said interior space;

a plunger advancably disposed in said barrel member; and means for rotatably connecting said housing and said barrel member for rotation of said barrel member in a fixed longitudinal position with respect to said housing, whereby said barrel member with said pressure gauge is rotatable to a desired position relative to said housing.

11. A syringe assembly according to claim 10, wherein said means for rotatably connecting comprises means for connecting said barrel member and said housing for rotation of said barrel member relative to said housing in a single longitudinally fixed position with respect to said housing and wherein said plunger is advancably associated with said housing, whereby rotation of said barrel member does not result in longitudinal movement of said barrel member relative to said plunger.

12. A syringe assembly according to claim 10, wherein said means for rotatably connecting comprises means for connecting said barrel member and said housing in a longitudinally fixed position of said barrel member relative to said housing wherein said barrel member is rotatable relative to said housing without longitudinal movement out of said longitudinally fixed position.

13. A syringe assembly according to claim 10, wherein said means for rotatably connecting comprises a ridge positioned in a single plane on one of said housing and said barrel member, and a groove positioned in a single plane on the other of said housing and said barrel member, said groove receiving said ridge whereby said barrel member is rotatably connected to said housing, and rotation of said barrel member relative to said housing does not result in longitudinal movement of said barrel member relative to said housing.

14. A syringe assembly according to claim 10, further comprising means mounted within said housing for advancing said plunger relative to said barrel member, whereby said barrel member is rotatable relative to said housing without advance of said plunger relative to said barrel member.

* * * * *